(12) United States Patent
Forsythe et al.

(10) Patent No.: US 6,521,670 B1
(45) Date of Patent: Feb. 18, 2003

(54) INSECT CONTROL METHOD AND COMPOSITION

(75) Inventors: Darol Forsythe, Boise, ID (US); John M. Forsythe, Nampa, ID (US); Ralph I. Freudenthal, West Palm Beach, FL (US)

(73) Assignee: BioAdvantage, Inc., Meridian, ID (US)

( * ) Notice: Subject to any disclaimer, the term of this patent is extended or adjusted under 35 U.S.C. 154(b) by 0 days.

(21) Appl. No.: 09/657,381

(22) Filed: Sep. 8, 2000

(51) Int. Cl.⁷ .................. A01N 27/00; A61K 31/015
(52) U.S. Cl. ..................................................... 514/765
(58) Field of Search ................... 514/700, 765

(56) References Cited

U.S. PATENT DOCUMENTS 2,347,265 A    4/1944  Hyman
3,080,278 A    3/1963  Douros, Jr. et al.
5,459,122 A   10/1995  Ford et al.

FOREIGN PATENT DOCUMENTS

EP   0087269      *   2/1983
JP   62045502     *   2/1987

* cited by examiner

*Primary Examiner*—Alton Pryor
(74) *Attorney, Agent, or Firm*—TraskBritt

(57) ABSTRACT

A method and composition for controlling insects is disclosed. A method and composition are most effective for killing insect populations in enclosed spaces, although direct contact with insects may also be effective. The method involves exposing the insects to 1,4-dimethylnaphthalene for a sufficient period of time to cause death to the same, wherein the insects may then be more readily destroyed. In enclosed spaces which are to be disinfected, a mist or vapor of 1,4-dimethylnaphthalene may be diffused into the space with the space sealed for a sufficient period of time to eliminate insects.

15 Claims, No Drawings

INSECT CONTROL METHOD AND COMPOSITION

BACKGROUND OF THE INVENTION

1. Field of the Invention

The instant invention relates generally to the fields of biology and chemistry. More particularly, the present invention relates to novel insecticidal compounds, compositions thereof, and to methods of controlling (e.g., reduction or elimination) insects therewith.

2. State of the Art

Many ingredients are known for their insect repellant and killing properties. Most of these insecticides are toxic or harmful to human beings animals, and agricultural products, and are used in large amounts as insecticides. Because of environmental and regulatory considerations, the usage of insecticides are under increasing scrutiny with regards to such matters as toxicity, carcinogenicity, and air and ground water contamination. Some commercially-available insecticides have had their uses curtailed because of such considerations.

In an effort to address these considerations, in particular concerns regarding toxicity, a number of insecticides have been developed. One such insecticide is described in U.S. Pat. No. 2,347,265, issued to Hyman ("the Hyman Patent"). The Hyman Patent describes preparation of insecticidal substances from raw materials containing alkyl substituted derivatives of naphthalene, which are found naturally occurring as minor components of mineral oils. These substances are isolated in small amounts from cracked fuel oils used commercially. As described and claimed in the Hyman Patent, the insecticidal compositions must be present in the oil phase of a prepared insecticide in order for the alkylated naphthalene contained therein to exhibit insecticidal activity. Additionally, the insecticidal compositions contain a mixture of substituted derivatives (i.e., a mixture of various isomers of substituted naphthalenes).

The insecticidal compositions of the Hyman Patent, however, are undesirable for use on plants or in agricultural settings, such as the storage of harvested crops (e.g., stored potatoes or grains). For example, use of oils on plants and stored agricultural products can accelerate production of molds, affect plant physiology (e.g., respiration), affect the taste of plants and agricultural products ultimately used as food products, stain stored agricultural products, and make the surface of the plant or agricultural product (including facilities storing the agricultural products or residential buildings having treated plants) sticky and susceptible to globing or coating with undesirable dust or contaminants. Also undesirable, from an environmental and regulatory standpoint, is that the Hyman Patent utilizes a "mixture" of substituted naphthalenes, some of which have characteristics relating to toxicity, effectiveness, and environmental contamination which are variable and, in some instances, unknown. With regard to variability, U.S. Pat. No. 3,080,278, issued to Douros et al., describes use of substituted naphthalenes as fungal growth inhibitors. As recognized therein, various isomers of dialkylnaphthalenes are inactive, whereas various mixtures of selected substituted naphthalenes, tested at the same concentration levels and under the same conditions, act as effective fungal growth inhibitors To same effect, in U.S. Pat. No. 5,459,122, issued to Ford et al. ("the Ford Patent") there is described improved aromatic oil compositions containing naphthene-benzenes and dinaphthenebenzenes, and additionally containing substituted naphthalenes. These oils, in addition to having insecticidal characteristics, also have phytotoxic properties making them suitable for use as herbicides. This, however, makes these oils undesirable for use on plants or many agricultural products.

In view of the shortcomings of the aforementioned compositions and methods known in the art, it would be advantageous to provide insecticidal compounds, compositions thereof, and methods of controlling insects therewith that are free from oil adjuvants or oil carriers. It would be further advantageous to provide an insecticide that has low toxicity to humans or animals, that is composed of a single isomer of a known compound, that is effective for use as an insect repellant or insecticide, that can be used in agriculture both during growth and after harvest in storage and transit, and which can be used in buildings occupied by humans and animals.

SUMMARY

A method, compound and composition for insecticidal uses has been discovered. Although various isomers and mixtures of isomers of the chemical dimethylnaphthalene have been used and suggested for various purposes, it now has been discovered that a particular isomer, 1,4-dimethylnaphthalene ("1,4-DMN"), is an effective insecticide. 1,4-DMN is effective when applied directly to insects, such as flies, moths, bees and the like, directly in liquid, or as a vapor or mist, and especially in confined spaces. 1,4-DMN is also effective when applied to or contained in various materials which is ingested by insects and when applied on plants, agricultural products, and food products. An insecticide formulation containing 1,4-DMN is effective in both low and high concentrations of 1,4-DMN in the formulation and when applied in low dosage and in high dosage rates. A significant advantage of 1,4-DMN is that it has low toxicity in humans and animals and may be used in contact with agricultural and food products. A further advantage of the insecticidal compounds and compositions of the present invention is that they are preparations which include substantially pure 1,4-DMN either alone or in combination with oil-free solvents.

DETAILED DESCRIPTION OF THE INVENTION 1,4-DMN in pure form and insecticidal compositions including 1,4-DMN in an oil-free solvent or carrier is effective as an insecticide. 1,4-DMN and formulations containing the same may be applied directly to insects, plants, agricultural products, and food products. The use of 1,4-DMN is particularly advantageous inasmuch as it has low toxicity in humans and animals. Because many plants and food products, such as potatoes, contain 1,4-DMN as a volatile material, the effect on insects is particularly surprising.

The 1,4-DMN and formulations thereof may be applied in any known form, such as, for example, liquid form, as a vapor, or as a mist. 1,4-DMN may be used in the traditional manner in which insecticides are utilized. For example, it may be applied to surfaces which have another ingredient that attracts insects, e.g., fly strips. Alternatively, it may be incorporated into compositions which are sources for insects, e.g., honey-sugar water or other formulations which may be ingested by insects. Thus, DMN may be utilized in a large number of areas and means as an insecticide.

The main advantage of 1,4-DMN as an insecticide is that it is effective and has relatively low toxicity. Thus, it may be incorporated in materials, which when contacted by humans or animals, would not be harmful to them. Additionally, 1,4-DMN may be safely applied to plants, agricultural products, and food products (e.g., stored potatoes and grains). Because of its relatively low toxicity, 1,4-DMN may also be applied within structures inhabited by animals and/or humans (e.g., residential homes).

In experiments conducted with vaporized 1,4-DMN, it was noted that flies, bees, wasps, and other winged insects contained within a potato storage facility were killed or placed in a state of stupor. The concentration of vapor of 1,4-DMN in the atmosphere of the storage facility was rather low. The storage facility had a volume of approximately 10,000 cubic feet and a head space of about 9,000 cubic feet (approximately 1,000 cubic feet of potatoes being contained in the facility). In the experiment, 500 milliliters and 188 milliliters of 1,4-DMN were vaporized and used. Both concentrations were effective. The facility was in a closed state for about 48 hours.

The specific gravity of DMN is close to one, so that the above dosage rates may be expressed as $ml/m^3$ or $gm/m^3$. Dosage rates as low as 0.1 $gm/r^3$ may be generally effective for the purposes of the invention. The dosage may be expressed in parts per million (ppm). One $ml/m^3$ equals one ppm. Thus, the preferred dosage rates for the instant invention may be from 0.1 ppm to about 2 ppm. Lower and higher dosage rates may be used depending upon time of exposure and the like.

The ventilation system of the storage facility had been shut off so that there was no fresh air entering the building and the building was not being evacuated during the 1,4-DMN vapor treatment. The effect of the 1,4-DMN on insects within the storage facility was fairly immediate with substantially all the insects being killed within about 24 hours. In regions or facilities with dangerous insects, or where there is a large concentration of less-dangerous insects, such as bees, wasps and the like, which would create risks to workers, a closed facility may be treated to make it safe. Dangerous insects such as spiders, scorpions and the like may also effectively be treated in this manner with 1,4-DMN.

A concentrated 1,4-DMN composition including pure 1,4-DMN or solutions or potions or mixtures containing a high concentration of 1,4-DMN may be readily utilized to treat homes, office buildings, and the like to prevent infestation by insects and the like. Thus, cockroaches, spiders, millipedes, centipedes and the like may be killed by 1,4-DMN via traditional fumigation or spray methods that are currently in use by office buildings, houses, and the like. The significant advantage of 1,4-DMN, again, is that it less toxic to humans and plants. An additional advantage is that the compound and formulations of the present invention do not contain oil adjuvants or oil solvents, making them more suitable for use on plants and less destructive to furnishings and interior surfaces of the aforementioned structures.

As previously suggested, in addition or in place of application of substantially pure 1,4-DMN, various compositions including 1,4-DMN therein may be used to combat and control infestations of insects. The insects which may be combated and controlled by the use of the invention compounds include those associated with agriculture (which term includes the growing of crops for food and fiber products, horticulture and animal husbandry), forestry, the storage of products of vegetable origin, such as fruit, grain and timber, and also those insects associated with the transmission of diseases of man and animals.

Where application of 1,4-DMN to the locus of the insects is desired, compositions which include 1,4-DMN and one or more suitable inert diluent, carrier materials, and/or surface active agents are formulated and applied. The compounds of the invention may be the sole active ingredient of the composition or they may be admixed with one or more additional active ingredients such as insecticides, insecticide synergists, herbicides, fungicides or plant growth regulators where appropriate. Suitable additional active ingredients for inclusion in admixture with the compounds of the invention may be compounds which will broaden the spectrum of activity of the compounds of the invention or increase their persistence in the location of the insect. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include materials such as pyrethroids, organophosphates, carbamates (including aryl carbamates), benzoyl ureas, organic tin compounds, macrolides, hormones, pheromones, and organochlorine compounds.

In addition to the major chemical classes of insecticide listed above, other insecticides having particular targets may be employed in the mixture if appropriate for the intended utility of the mixture. For instance, selective insecticides for particular crops can be employed. Alternatively insecticides specific for particular insect species/stages for example ovolarvicides such as clofentezine, flubenzimine, hexythiazox and tetradifon, motilicides such as dicofol or propargite, acaricides such as bromopropylate, chlorobenzilate, or insect growth regulators such as hydramethylon, cyromazin, methoprene, chlorofluazuron and diflubenzuron may also be included in the compositions.

Examples of suitable insecticide synergists for use in the compositions include piperonyl butoxide, sesamex, and dodecyl imidazole. Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insects to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as aerosols, dips or sprays.

Dips and sprays are generally aqueous dispersions or emulsions of the active ingredient in the presence of one or more known wetting agents, dispersing agents or emulsifying agents (surface active agents). Aerosol compositions may contain the active ingredient or ingredients, a propellant and an inert diluent, for example odorless kerosene or alkylated benzenes. Where liquid formulations are desirable, liquid extenders, diluents, or carriers of a non-reactive nature can be utilized. Examples of such materials include aliphatic alcohols, chlorocarbons, ketones, glycols, and aromatic hydrocarbons, among others.

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropyl-naphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may alternatively be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, methylnaphthalene, xylenes and trichloroethylene, N-methyl-2-pyrrolidone and tetrahydrofurfuryl alcohol (THFA), among others.

The compositions which are to be used in the form of aqueous dispersions or emulsions are generally supplied in the form of a concentrate containing a high proportion of 1,4-DMN, which may be diluted with water before use. These concentrates are often required to withstand storage for prolonged periods and after storage, to be capable of dilution with water to form aqueous preparations which remain homogenous for a sufficient time to enable them to be applied by conventional spray equipment. The concentrates may contain 10–99% by weight of the active ingredient or ingredients. When diluted to form aqueous preparations such preparations may contain varying amounts of the active ingredient depending upon the purpose for which they are to be used.

In use, the compositions are applied to the insects, to the locus of the insects, to the habitat of the insects, to growing plants, or to agricultural/food products liable to infestation by the insects, by any of the known means of applying insecticidal compositions, for example, by spreading, dusting or spraying. The compositions of the invention can be applied to control or eliminate wide varieties of insects, including, for example, *Myzus persicae* (aphids), *Aphis fabae* (aphids), *Megoura viceae* (aphids), *Aedes aegypti* (mosquitos), Anopheles spp. (mosquitos), Culex spp. (mosquitos), *Dysdercus fasciatus* (capsids), *Musca domestica* (houseflies), *Pieris brassicae* (white butterfly, larvae), *Plutella maculipennis* (diamond back moth, larvae), *Phaedon cochleariae* (mustard beetle), *Tetranychus cinnabarinus* (carmine spider mite), *Tetranychus urticae* (red spider mites), Aonidiella spp. (scale insects), Trialeuroides spp. (white flies), *Blattella germanica* (cockroaches), *Periplaneta americana* (cockroaches), *Spodoptera littoralis* (cotton leaf worm), *Heliothis virescens* (tobacco budworms), *Chortiocetes terminifera* (locusts), Diabrotica spp. (rootworms), Agrotis spp. (cutworms), *Chilo partellus* (maize stem borers), and *Nilaparvata lugens* (plant hoppers), among others.

Although 1,4-DMN is effective alone as an insecticide, as discussed above, it may also be combined with other materials. For example, 1,4-DMN may be applied as a composition wherein 1,4-DMN is mixed in an atomizing mixture, preferably with a detergent which assists 1,4-DMN in staying dispersed. An emulsion of 1,4-DMN in water or other polar media may also be utilized. Alternatively, the water/1,4-DMN mixture may be intimately mixed immediately prior to application so that the 1,4-DMN is substantially distributed throughout the water medium.

1,4-DMN may also be intermixed with honey-sugar water or other materials which attract or are ingested by insects. Although, 1,4-DMN is a liquid, it has a relatively high boiling point such that it does not evaporate very quickly if utilized in insect food and exposed to the atmosphere for a considerable amount of time. Thus, it can retain its effectiveness for a long period of time even after being exposed to the atmosphere.

Additionally, 1,4-DMN may be absorbed into solid material wherein the solid material is then utilized as a source of 1,4-DMN, particularly in a confined space. Such solid material may provide sustained or controlled release of 1,4-DMN. For example, bananas are often shipped in boxes. When handling such boxes, unpacked boxes are exposed to the risks of spider bites, many of which bites may be dangerous. One such spider, the brown recluse spider, which is quite venomous and native to banana growing regions, arrives with banana shipments to the United States. At the packaging plant in a banana growing region, solid material containing 1,4-DMN may be placed in a box containing bananas whereby, upon evaporating, the 1,4-DMN would kill any spiders present in the box without harming the bananas.

In a different embodiment, 1,4-DMN may be absorbed into a powdery material which may then be dusted upon crops and the like for the purpose of killing beetles, aphids, and other crop damaging insects. It can similarly be used on house plants, as well as back-yard gardens and commercial crops. Of course, 1,4-DMN in either concentrated or dilute form can also be applied as a spray or mist to plants to prevent insect attack. Again, a significant advantage when applying to crops and trees which have fruits and vegetables about to be harvested is that the 1,4-DMN will not harm the fruit or vegetable or the plant or tree, and has reduced risk in human beings or animals who may later consume those fruits or vegetables. The exact mechanism by which 1,4-DMN is effective as an insecticide is not known. Given its lower toxicity towards humans and animals, it is surprising that 1,4-DMN has an effect upon insects.

Also, 1,4-DMN may be applied to various crops as they are being harvested to prevent insect damage during shipment and/or storage. The fact that 1,4-DMN is found in many crops such as potatoes and has a non-toxic behavior with regard to human being and animals renders it safe for applying to harvested crops which may be consumed after shortly so treated.

1,4-DMN has been found to be especially effective in closed spaces wherein the space has no significant ventilation and is treated with 1,4-DMN mist or vapor at low to high concentrations. Generally, it is preferred in such instances to apply pure 1,4-DMN as a mist wherein vapor form, although it may also be utilized in an aqueous mixture. Generally, it is preferred to not use solvents because they may introduce a toxicity factor which would otherwise not be present. A treated facility could be treated in a manner such that low concentrations 1,4-DMN were present as a vapor in the atmosphere. It may also be useful as an insecticide for household insects such as flies, moths, ants and the like.

What is claimed is:

1. A method of affecting the mortality of insects comprising contacting said insects with an effective amount of 1,4-dimethyl-naphthalene (1,4-DMN).

2. The method of claim 1, wherein said 1,4-DMN is in a liquid form having no oil adjuvants or solvents.

3. The method of claim 1, wherein said 1,4-DMN is a vapor (gas).

4. The method of claim 1, wherein said 1,4-DMN is substantially pure 1,4-DMN.

5. The method of claim 1, wherein said 1,4-DMN is present with an oil-free diluent.

6. The method of claim 1, wherein said 1,4-DMN is present with water.

7. The method of claim 3, wherein the vapor content of 1,4-DMN is at least about 0.1 $gm/r^2$.

8. The method of claim 3, wherein said 1,4-DMN vapor is present in a confined space .

9. A method of affecting the mortality of insects comprising contacting said inserts with an effective amount of 1,4-dimethyl-naphthalene (1,4-DMN), wherein said 1,4-DMN is a vapor (gas).

10. The method of claim 9, wherein said 1,4-DMN is in a liquid form having no oil adjuvants or solvents.

11. The method of claim 9, wherein said 1,4-DMN is substantially pure 1,4-DMN.

12. The method of claim 9, wherein said 1,4-DMN is present with an oil-free solvent.

13. The method of claim 9, wherein said 1,4-DMN is present with water.

14. The method of claim 9, wherein the vapor content of 1,4-DMN is at least about 0.1 $gm/m^2$.

15. The method of claims wherein said 1,4-DMN vapor is present in a confined space.

* * * * *

UNITED STATES PATENT AND TRADEMARK OFFICE
CERTIFICATE OF CORRECTION

PATENT NO.   : 6,521,670 B1
DATED        : February 18, 2003
INVENTOR(S)  : Darol Forsythe, John M. Forsythe and Ralph I. Freudenthal It is certified that error appears in the above-identified patent and that said Letters Patent is hereby corrected as shown below:

Column 3,
Line 22, change "gm/r$^3$" to -- gm/m$^3$ --

Column 8,
Line 4, change "gm/r$^3$" to -- gm/m$^3$ --
Line 8, change "inserts" to -- insects --

Signed and Sealed this

Sixth Day of May, 2003

JAMES E. ROGAN
*Director of the United States Patent and Trademark Office*